United States Patent [19]

Palomar et al.

[11] 4,449,520
[45] May 22, 1984

[54] PENILE PROSTHESIS DEVICE

[76] Inventors: Juan M. Palomar, 10 Southmoor Cir., NW., Kettering, Ohio 45429; Gary M. Bird, 510 Glenn Ave., New Carlisle, Ohio 45344

[21] Appl. No.: 414,568

[22] Filed: Sep. 2, 1982

[51] Int. Cl.³ ............................................... A61F 5/00
[52] U.S. Cl. ............................................. 128/79; 3/1
[58] Field of Search ................................... 128/79; 3/1

[56] References Cited

U.S. PATENT DOCUMENTS

| | | | |
|---|---|---|---|
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,235,227 | 11/1980 | Yamanaka | 128/79 |
| 4,318,396 | 3/1982 | Finney | 128/79 |
| 4,360,010 | 11/1982 | Finney | 128/79 |
| 4,364,379 | 12/1982 | Finney | 128/79 |
| 4,383,525 | 5/1983 | Scott et al. | 128/79 |

Primary Examiner—Stephen C. Pellegrino
Attorney, Agent, or Firm—Jacox & Meckstroth

[57] ABSTRACT

A pair of inflatable erecting tubes and a pair of inflatable reservoir tubes project from opposite ends of a pump unit including a rigid valve body molded as an insert within a pump body of resilient silicone material. The inflatable tubes are implanted within the right and left corpora cavernosa of the penis with the pump unit located at the base of the penis transecting the medial corporal septum. The valve body has a series of passages and spring biased one way valves which are effective to inflate the erecting tubes in response to the application of a squeezing pressure to opposite sides of the pump body and to delfate the erecting tubes in response to downward pressure on the pump body.

6 Claims, 9 Drawing Figures

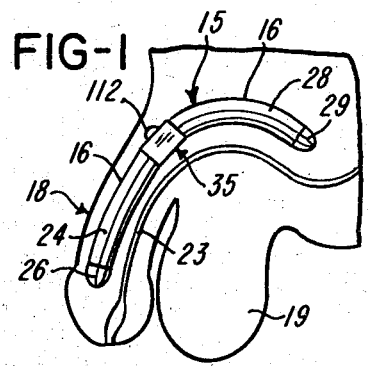
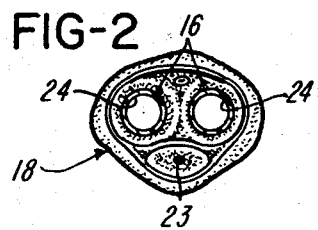
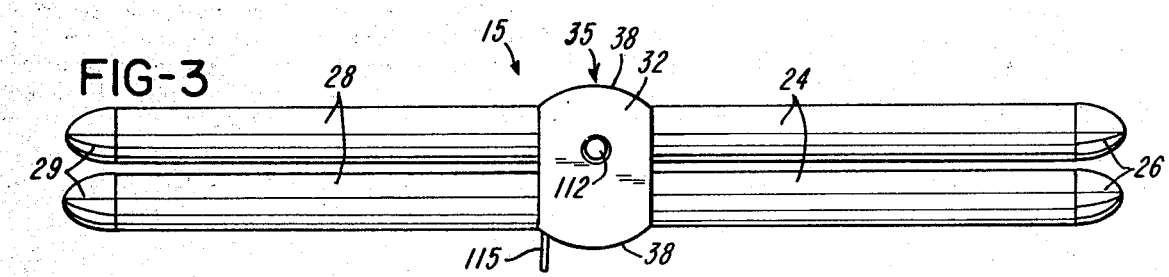
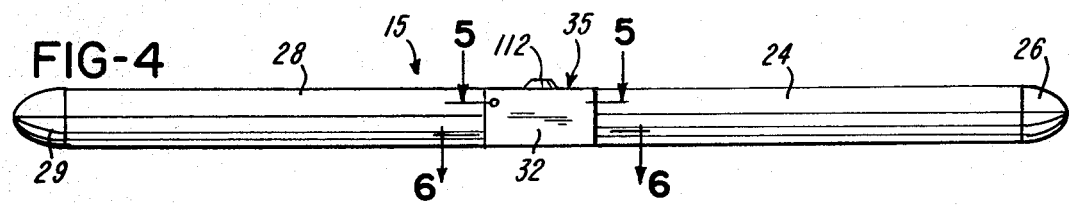
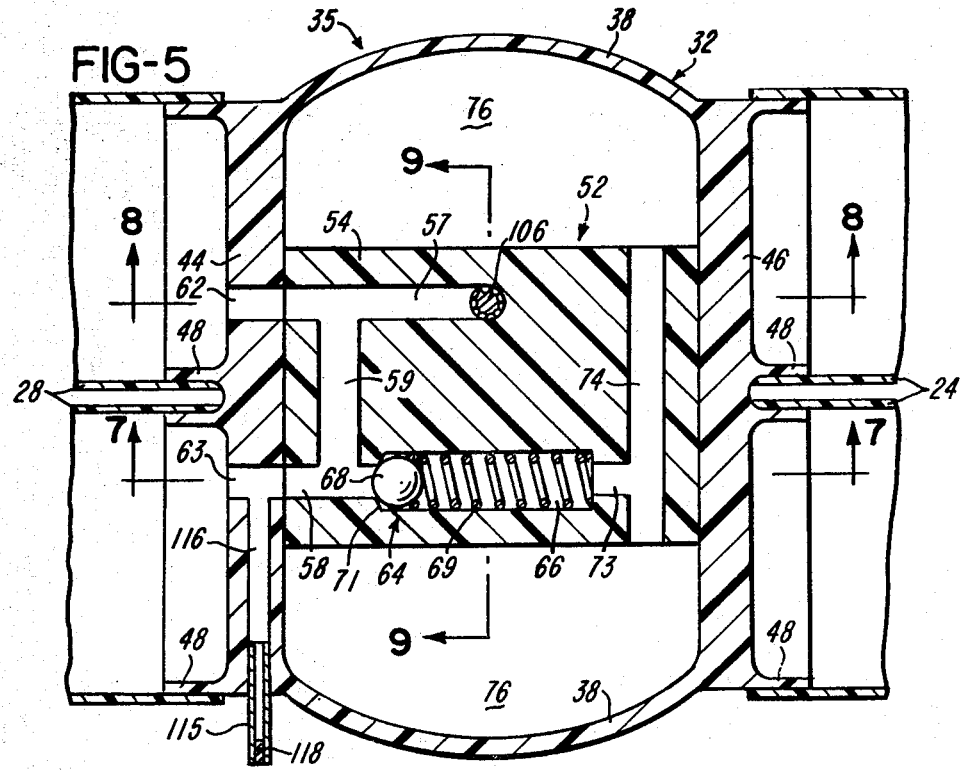

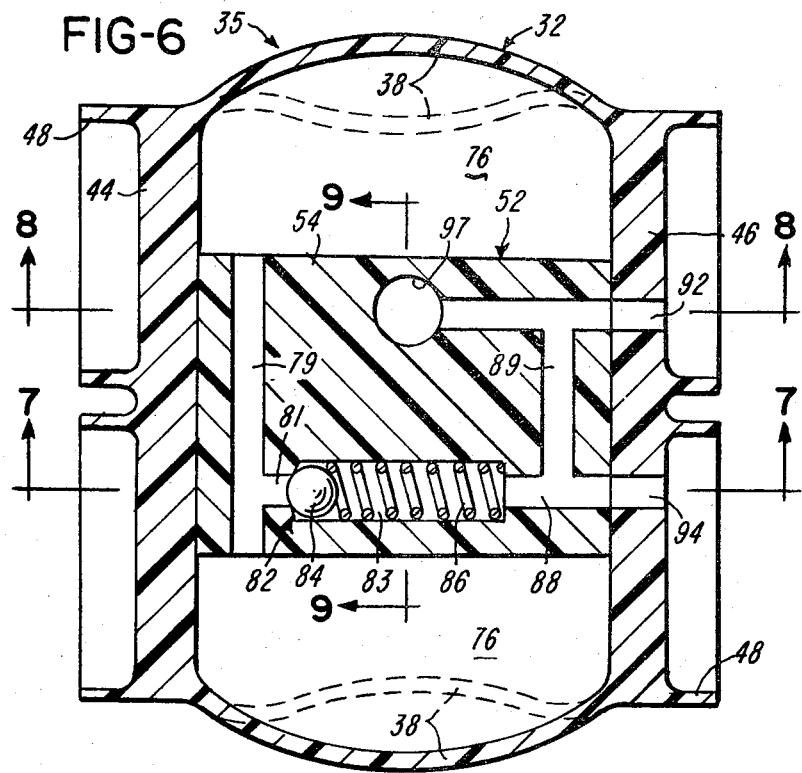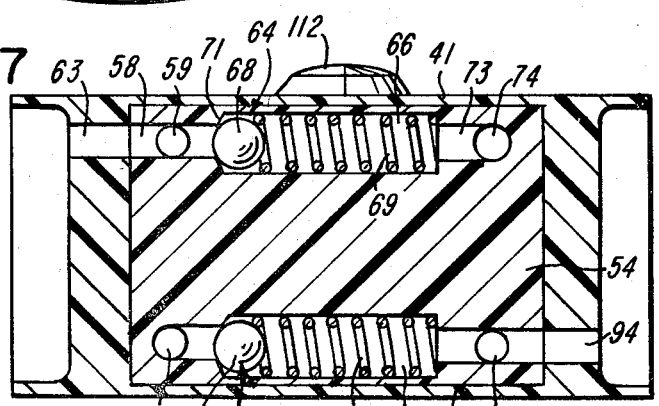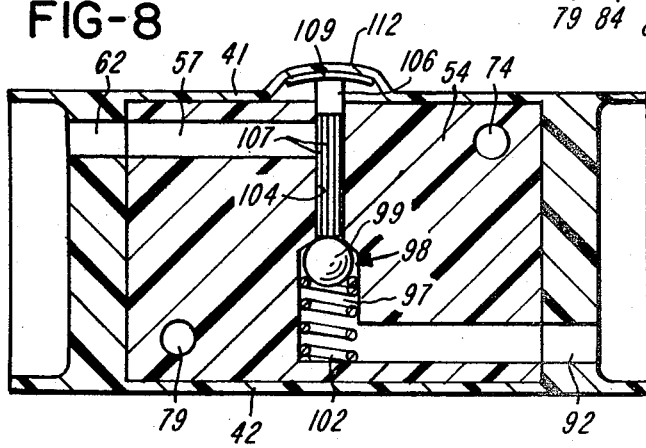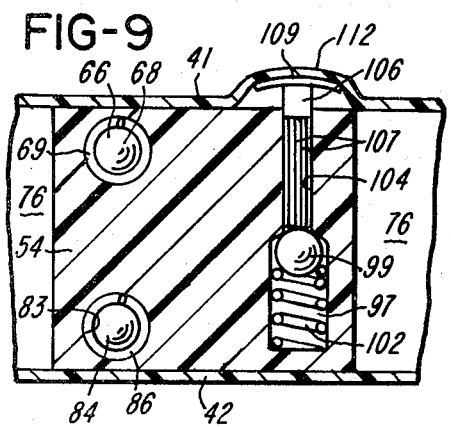

4,449,520

PENILE PROSTHESIS DEVICE

BACKGROUND OF THE INVENTION

In the treatment of male impotence, there have been a number of inflatable prosthesis devices which have been proposed and/or used such as, for example, the system disclosed in U.S. Pat. No. 3,954,102. In the prosthesis penile erection system disclosed in this patent, two elongated cylinders or tubes are formed of a silicone elastomer material, and the tubes are implanted within the right and left corpora cavernosa. A reservoir for the noncompressible fluid or liquid is implanted in the abdominal or pelvic cavity and is connected to the inflatable tubes by small silicone tubes which pass through a pump system implanted within the scrotum.

In order to avoid the implantation of a reservoir within the abdominal cavity, other forms of hydraulic implant devices have been proposed or used, for example, as disclosed in U.S. Pat. Nos. 4,009,711, 4,201,202, 4,235,227 and 4,318,396. In the latter U.S. Pat. No. 4,318,396, an implant embodiment is disclosed in connection with FIGS. 7-9, one for each of the two corpora cavernosa. The use of plural implants apparently avoids the need for further implants within the abdominal cavity and/or within the scrotum.

SUMMARY OF THE INVENTION

The present invention is directed to an improved penile prosthesis device which minimizes the number of parts and connections for the device or implant and significantly simplifies the surgical procedure for implanting the device within the corpora cavernosa. The device of the invention is not only convenient to operate but also avoids the discomfort which results from use of other devices which require pressing on sensitive skin tissue. The penile prosthesis device of the invention is also dependable in operation, minimizes the chances of malfunction and does not interfere with proper function of the male penis such as during urination and ejaculation.

In accordance with one embodiment of the invention, the above features and advantages are provided by an implant device which includes a pair of inflatable erecting tubes and a pair of inflatable reservoir tubes projecting from opposite ends of a compact pump unit. The entire implant device is located within the right and left corpora cavernosa with the pump unit located at the base of the penis at the level of the suspensory ligament and transecting the medial corporal septum. The pump unit incorporates a pump body having resilient opposite side walls and which encloses an insert valve assembly. Liquid is transferred or pumped from the reservoir tubes to the erecting tubes in response to lateral squeezing of the pump body to produce an erection of the penis. The erecting tubes are deflated by pressing downwardly on the pump unit at the base of the penis allowing the liquid within the erecting tubes to flow back or return directly to the reservoir tubes.

Other features and advantages of the invention will be apparent from the following description, the accompanying drawings and the appended claims.

BRIEF DESCRIPTION OF THE DRAWINGS

FIG. 1 shows a penile prosthesis device constructed in accordance with the invention and implanted within the right and left corpora cavernosa;

FIG. 2 is a cross-section of the penis illustrated in FIG. 1 and showing the location of the erecting tubes;

FIG. 3 is a top plan view of the implant device shown in FIG. 1 and at approximately full scale;

FIG. 4 is a side elevational view of the implant device shown in FIG. 3;

FIG. 5 is a greatly enlarged section of the pump unit forming part of the implant device of the invention and taken generally on the line 5—5 of FIG. 4;

FIG. 6 is a section similar to FIG. 5 and taken generally on the line 6—6 of FIG. 4;

FIG. 7 is a section of the pump unit as taken generally on the line 7—7 of FIGS. 5 and 6;

FIG. 8 is a section as taken generally on the line 8—8 of FIGS. 5 and 6; and

FIG. 9 is a fragmentary section as taken generally on the line 9—9 of FIGS. 5 and 6.

DESCRIPTION OF THE PREFERRED EMBODIMENT

As illustrated in FIG. 1, a penal prosthesis device 15 constructed in accordance with the invention is implanted in the right and left corpora cavernosa 16 of the penis 18 and extends into the root portions or crura of the corpora cavernosa above the scrotum 19. As will be explained later, the device 15 is implanted by making an incision at the top of the base of the penis so that there is no disturbance or interference with the urethra 23.

Referring to FIGS. 3 and 4, the prosthesis device 15 includes a pair of inflatable erecting cylinders or tubes 24 which have rounded and closed forward tip or end portions 26. The device also includes a pair of flexible and inflatable reservoir cylinders or tubes 28 which have rounded closed rearward tip or end portions 29. The tubes 24 and 28 are preferably formed or molded of a silicone elastomer which is compatible with body tissue, and the elastomer is also used for forming or molding a centrally located pump body 32 forming part of a pump unit 35. The pump body 32 connects the forward ends of the reservoir tubes 28 to the rearward ends of the erecting tubes 24 and is bonded to the tubes to form a positive fluid-tight seal. It is also within the scope of the invention to mold the tubes 24 and 28 as an integral part of the pump body 32, after which the separately molded end portions 26 and 29 are bonded or fused to the outer ends of the hollow tubes 24 and 28, respectively.

As shown in FIGS. 5-9, the body 32 of the pump unit 35 includes opposite resilient side walls 38 which are integrally connected by a top wall 41 (FIG. 9) and a bottom wall 42. The walls 38, 41 and 42 integrally connect opposite end walls 44 and 46 (FIG. 5) which are molded substantially thicker than the side walls 38. A pair of cylindrical projections 48 are also molded as an integral part of the pump body walls 44 and 46 and project into the corresponding tubes 24 and 28. The projections 48 are heat fused or adhesively bonded to the inner surfaces of the tubes 24 and 28 to form a fluid-tight seal and a positive connection for each of the tubes with the pump body 32.

As also shown in FIGS. 5-9, the pump body 32 encloses or surrounds a valve assembly 52 which includes a rectangular valve body 54 preferably formed of a rigid plastics material having a higher melting point than the silicone elastomer material forming the pump body 32. The valve assembly 52 is placed as an insert within the mold cavity for the pump body 32 so that the opposite end walls 44 and 46 of the pump body and the top wall 41 and bottom wall 42 are heat fused or bonded to the valve body 54 during the molding operation of the valve body.

Referring to the section view of in FIG. 5, the upper portion of the valve body 54 has a set of parallel passages 57 and 58 which are connected by a cross passage 59 and which align with corresponding passages 62 and 63 molded within the rearward end wall 44 of the pump body 32. The passage 58 extends to a one way check valve 64 formed by an enlarged chamber 66 which receives a spherical valve member or ball 68. A compression spring 69 is also confined within the chamber 66 and urges the ball 68 towards a tapered valve seat 71 to form a normally closed valve. The chamber 66 is connected to a passage 73 to a cross passage 74 which connects right and left pump chambers 76 defined between opposite sides of the valve body 54 and the outer resilient walls 38 of the pump body 32.

In the lower portion of the pump unit 35 (FIG. 6), the valve body 54 has a lower cross passage 79 which also connects the pump chambers 76 and is connected by a port or passage 81 to a lower one way check valve 82 having a valve chamber 83 which also receives a spherical valve member or ball 84 and a compression spring 86 to form a normally closed valve. A passage 88 connects the valve chamber 83 with a cross passage 89 which, in turn, connects with parallel passages 92 and 94 extending through the front end wall 46 of the pump body 32 to the erecting tubes 24.

The passage 92 (FIG. 6) within the valve body 54 extends to the lower end of a vertical valve chamber 97 (FIG. 8) of a release valve 98. The chamber 97 receives a spherical valve member or ball 99 and a compression spring 102 to form another normally closed one-way valve. The valve chamber 97 is connected by a vertical port or passage 104 to the upper passage 57 (FIG. 5) within the valve body 54. The passage 104 receives the stem of a manually operated released valve actuator 106 which has axially extending grooves 107 forming peripherally spaced fluid passages to connect the valve chamber 97 to the passage 57 when the valve 98 is opened. The valve actuator 106 has a head portion 109 which projects upwardly from the top surface of the valve body 54 but remains covered by an upwardly projecting portion 112 of the top wall 41 of the pump body 32.

The implantation of the prosthesis device 15 is made by making an incision over the synphysis pubis at the base of the penis. The subcutaneous tissue is dissected preserving the suspensory ligament of the penis in the midline. The tunica albuginea of the right and left corpora cavernosa is exposed, and an incision is made on the lateral aspect of the right and left corpora. Rigid metal dilators are used to develop distal and proximal cavities within the right and left corpora cavernosa, and an opening or window is made in the mid septum of the corpora cavernosa to open a continuous passage connecting the right and left sides.

A Furlow carrier device is used to insert or pull the left erecting cylinder or tube 24 through the open septum between the two corporas and into the left corpora, and then the right erecting tube 24 is advanced or pulled into the right corpora in the same manner. The left reservoir tube 28 is then passed through the window within the septum and placed in the left crura. This locates the pump unit 35 within both the right and left corpora with the midline septum of the corpora holding the center portion of the pump unit 35 at the base of the penis. Finally, the right reservoir tube 28 is placed into the right crura.

After the device 15 is implanted, an isotonic solution such as a normal saline or isotonic radiopaque solution, is inserted into the device through a tube 115 (FIG. 5) which is connected by a passage 116 to the passage 63 within the rearward end wall 44 of the pump body 32. The tube 115 projects from the right side after the lateral openings within the corpora are closed with a nonabsorbable monofilament suture. A blunt needle of a syringe is inserted into the tube 115 for filling the device with a predetermined volume of the solution, after which the tube 115 is sealed by a stainless steel plug 118. The opening within the skin over the plug 118 is closed after the filling with a monofilament suture to prevent dislodgement of the plug 118.

In operation of the prosthesis device 15, when the patient desires to produce an erection, he lightly and repetitively compresses or pinches the side walls 38 of the pump body 32 at the base of the penis. As the side walls 38 are deformed inwardly, as illustrated by the dotted lines in FIG. 6, the liquid within the chambers 76 is displaced into the passage 79 (FIG. 6) past the one way check valve 82 and into the erecting tubes 24 through the passages 88, 89, 92 and 94. When the squeezing of the side walls 38 is released for return to their normal positions (FIG. 5), the suction within the chambers 76 causes liquid from the reservoir tubes 28 to pass through the passages 62, 63, 58 and 59 past the one way check valve 64 and into the pump chambers 76 through the passages 73 and 74. Thus repetitive light squeezing of the side walls 38 progressively transfers the liquid or solution from the reservoir tubes 28 to the erecting tubes 24 until the erecting tubes 24 produce the desired degree of stiffness or penile firmness.

When it is desired to deflate the erecting tubes 24 for detumesence, the patient simply presses downwardly with a light pressure on the base of the penis to depress the release valve actuator 106 downwardly to unseat the spherical valve member or ball 99. When the release valve 98 is open, the liquid within the erecting tubes 24 flows inwardly through the passages 92, 94, 89 and upwardly through the passage 104 (FIG. 8) to the passage 57 so that the liquid returns directly into the reservoir tubes 28 through the passages 58, 59, 62 and 63. The filling tube 115 may also be connected to an auxiliary reservoir bag or container located within the scrotum 19 in the event the reservoir tubes 28 can not hold the desired volume of solution.

From the drawings and the above description, it is apparent that a penile prosthesis device constructed in accordance with the present invention provides desirable features and advantages. As one important feature, the device is convenient to operate or use and avoids discomfort by providing for pressing the relatively thicker tissues at the base of the penis for producing either an erection or detumesence. The unitary device of the invention is also easy to implant so that the surgical procedure is simplified, and hospitalization is shortened. The device further provides for dependable and long operational life with a minimum chance of malfunction and does not interfere with proper function of the penise, such as urination or ejaculation. In addition the prosthesis device 15 is simple to manufacture with the valve assembly 52 being inserted into the mold for the pump body 32 to produce the pump unit 35. Also, the simplified operation of the device minimizes the medical supervision required after the immediate postoperative period.

While the form of implant device and its method of construction herein described constitute a preferred embodiment of the invention, it is to be understood that the invention is not limited to this precise form of implant and method, and that changes may be made therein without departing from the scope and spirit of the invention as defined in the appended claims. It should also be understood that the valve chambers 66, 83, and 97 and cross passages 59 and 82 are originally formed within the valve body 54 so that they extend to outer surfaces of the body. The passages 59 and 89 and the chamber 97 are then closed by solid plugs (not shown) and tubular plugs (not shown) form the ends of the chambers 66 and 83 and define the passages 73 and 88. It is further within the scope of the invention to form or mold the reservoir tubes and/or erecting tubes with a non-uniform wall thickness or with internal ribs. For example, the reservoir tubes 28 may be molded with the upper and lower portions of each tube with a heavier wall thickness or with internal ribs to prevent full collapsing of the tubes and to provide column strength when the tubes 28 are partially collapsed during erection.

The invention having thus been described, the following is claimed:

1. A penile prosthesis device adapted to be implanted in the right and left corpora cavernosa to provide for a mechanical erection, said device comprising a pump unit adapted to be implanted at the base of the penis transecting the medial corporal septum, said pump unit having a forward end and a rearward end, a pair of separate erecting tubes of flexible material and extending from said forward end of said pump unit, a pair of separate reservoir tubes of flexible material and extending from said rearward end of said pump unit, said erecting and reservoir tubes being adapted to receive a noncompressible liquid, said pump unit including a valve body defining a first set of passages connected to both of said reservoir tubes and a second set of passages connected to both of said erecting tubes, said pump unit defining an inlet passage extending from said first set of passages and adapted to be connected to an auxiliary liquid supply container located within the scrotum, a set of one way valves located within said first and second sets of passages, laterally actuating pump means effective to pump liquid from said reservoir tubes and said inlet passage through said first set of passages to said second set of passages and said erecting tubes for pressurizing said erecting tubes in response to the application of squeezing pressure laterally to opposite sides of the penis at the base, a return passage connecting said first and second sets of passages, and said pump unit including a pressure release valve within said return passage and effective to release the pressure of the liquid within both said erecting tubes for return of the liquid to both said reservoir tubes through said first and second set of passages.

2. A prosthesis device as defined in claim 1 wherein said pump unit comprises a pump body having opposite resilient side walls adapted to be deformed inwardly in response to the application of the squeezing pressure, said valve body is disposed between said side walls of said pump body and cooperates therewith to define separate pumping chambers on opposite sides of said valve body, and said first and second sets of passages connect said reservoir and erecting tubes to said pumping chambers.

3. A prosthesis device as defined in claim 2 wherein said first and second sets of passages comprise cross passages within said valve body and connected said pumping chambers.

4. A penile prosthesis device adapted to be implanted in the right and left corpora cavernosa to provide for a mechanical erection, said device comprising a pump unit adapted to be implanted at the base of the penis transecting the medial corporal septum, said pump unit including a forward end and a rearward end, a pair of separate erecting tubes of flexible material and connected to said forward end of said pump unit, a pair of separate reservoir tubes of flexible material and connected to said rearward end of said pump unit, said erecting and reservoir tubes being adapted to receive a noncompressible liquid, said pump unit including a pump body defining a pumping chamber and enclosing a substantially rigid valve body, said valve body defining a first passage connecting both of said reservoir tubes together and a second passage connecting both of said erecting tubes together, said valve body further defining a third passage connecting said first passage to said pumping chamber, a fourth passage connecting said second passage to said pumping chamber, a fifth passage connecting said first and second passages, a set of one-way valves disposed within said third and fourth passages, said pump body further including a resilient wall cooperating with said valves for pumping liquid from said reservoir tubes through said passages to said erecting tubes, and a pressure release valve within said fifth passage for returning the liquid from both said erecting tubes through said passages to both said reservoir tubes.

5. A prosthesis device as defined in claim 4 wherein said pump body has opposite resilient side walls defining right and left pump chambers separated by said valve body, and said third and fourth passages connect said right and left pump chambers.

6. A prosthesis device as defined in claim 4 wherein said first and third passages are disposed within an upper portion of said valve body, said second and fourth passages ae disposed within a lower portion of said valve body, and said fifth passage extends generally vertically within said valve body.

* * * * *